United States Patent [19]

Flagg

[11] 4,250,309
[45] Feb. 10, 1981

[54] HALOGENATED ALKENYL ISOCYANURATE COMPOUNDS

[75] Inventor: Edward E. Flagg, Midland, Mich.

[73] Assignee: The Dow Chemical Company, Midland, Mich.

[21] Appl. No.: 80,967

[22] Filed: Oct. 1, 1979

Related U.S. Application Data

[63] Continuation-in-part of Ser. No. 10,300, Feb. 8, 1979, abandoned.

[51] Int. Cl.³ .......................................... C07D 251/34
[52] U.S. Cl. .................................................. 544/221
[58] Field of Search ........................................ 544/221

[56] References Cited

U.S. PATENT DOCUMENTS

| 2,947,736 | 8/1960 | Lundberg | 544/221 |
| 3,470,228 | 9/1969 | Heinert | 544/221 |

FOREIGN PATENT DOCUMENTS

| 1159461 | 12/1963 | Fed. Rep. of Germany | 544/221 |
| 42-9345 | 5/1967 | Japan | 544/221 |
| 51-13784 | 2/1976 | Japan | 544/221 |
| 1022670 | 3/1966 | United Kingdom | 544/221 |
| 381668 | 8/1973 | U.S.S.R. | 544/221 |

*Primary Examiner*—John M. Ford
*Attorney, Agent, or Firm*—Douglas N. Deline

[57] ABSTRACT

New and useful halogenated alkenyl isocyanurate compounds of the formula

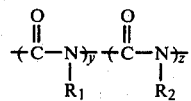

wherein $R_1$ and $R_2$ are specified substituents are formed by reacting a halogenated isocyanurate compound with a di- or polyolefin.

6 Claims, No Drawings

HALOGENATED ALKENYL ISOCYANURATE COMPOUNDS

CROSS-REFERENCE TO RELATED APPLICATION

This is a continuation-in-part of prior copending application Ser. No. 010,300, filed Feb. 8, 1979, now abandoned.

BACKGROUND OF THE INVENTION

This invention comprises novel halogenated alkenyl isocyanurate compounds. In the prior art a limited number of alkenyl isocyanurate compounds have already been prepared. For instance triallylisocyanurate was prepared by Tanimoto et al. by the reaction of 3-bromopropene with methylformamide and potassium isocyanate. Additional known alkenyl isocyanurate compounds include trimethallyl isocyanurate, and tris(1,3-pentadienyl)isocyanurate. Heinert disclosed in U.S. Pat. No. 3,480,627 a method for preparing tri(1-alkenyl-)isocyanurates including trivinyl isocyanurate and tripropenyl isocyanurate.

Halogenated alkyl isocyanurates have generally been prepared by addition of halogen to isocyanurates containing unsaturated substituents or by nucleophilic substitution of previously prepared alkyl isocyanurates. A third method, disclosed by Muller et al. in U.S. Pat. No. 3,259,626 is the trimerization of a halo-substituted isocyanate.

SUMMARY OF THE INVENTION

The invention relates to new and useful isocyanurate compounds and in particular is concerned with novel halogenated alkenyl isocyanurate compounds corresponding to the formula $$\left(\begin{matrix} O \\ \parallel \\ -C-N- \\ | \\ R_1 \end{matrix}\right)_y \left(\begin{matrix} O \\ \parallel \\ -C-N- \\ | \\ R_2 \end{matrix}\right)_z \quad (I)$$

wherein:
(a) $R_1$ is selected from

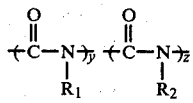

wherein R' is hydrogen or a $C_{1-10}$ radical selected from alkyl, alkenyl, and oxo-, halo- or alkyl-substituted derivatives thereof; R" is a $C_{2-10}$ radical selected from alkyl, alkenyl and oxo-, halo-, or alkyl-substituted derivatives thereof, provided that at least one of R' or R" is alkenyl or an oxo-, halo-, or alkyl-substituted derivative thereof; R''' is a $C_{3-10}$ divalent radical containing ethylenic unsaturation selection from acyclic, cylic and multicyclic alkenediyls and alkyl-, halo- or oxo-derivatives thereof; X is halogen;

(b) $R_2$ is a $C_{1-8}$ radical selected from alkyl, haloalkyl and aryl; and (c) y is an integer from 1 to 3; and z is an integer from 0 to 2, provided that y+z equals 3.

The compounds possess fungicidal properties and may be used as cross-linking additives in polymers.

DETAILED DESCRIPTION OF THE INVENTION

The compounds of this invention of formula I are produced by reaction of mono-, di- or trihalo isocyanurates or mixtures thereof with a diolefin or polyolefin or mixtures thereof. Preferred isocyanurate reactants are halogenated isocyanurates of the formula

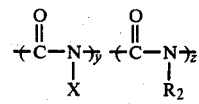

wherein X is halogen and $R_2$, y and z are as previously defined.

Examples of suitable isocyanurate compounds include trichloro isocyanurate, (1,3,5-trihalo-s-triazine-2,4,6-trione), N-benzyl dichloro isocyanurate (1-phenyl-3,5-dihalo-s-triazine-2,4,6-trione), N,N-dimethyl chloroisocyanurate (1,3-dimethyl-5-halo-s-triazine-2,4,6-trione), and the like.

Particularly preferred isocyanurate reactants are those wherein X in the above is chlorine.

The olefin reactant is an ethylenically unsaturated compound containing at least two double bonds. Optionally it may be further substituted with alkyl-, halo- or oxo-substituents. The compound may be cyclic, acyclic or multicyclic and suitably contains from 4 to 22 carbons. The olefin reactant may be depicted diagrammatically as having the formula

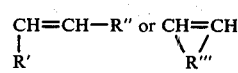

wherein R', R" and R''' are as previously defined. Preferred as a second reactant are cyclic or acyclic alkadienes of from 4 to 10 carbons.

Examples of suitable second reactants include butadiene, 1,3-pentadiene, 1,4-pentadiene, cyclopentadiene, 1,4-cyclohexadiene, dicyclopentadiene, 1-chlorobutadiene, 1,4-dichlorocyclopentadiene, 4-methyl-1,3-pentadiene, 2,5-cyclohexadiene-1,4-dione, and the like.

A most preferred acyclic olefin reactant is an alkadiene having one ethylenically unsaturated bond in the α position. Reactions of such compounds with an above-described isocyanurate reactant proceed at a relatively rapid rate because of the absence of steric hindrance that would be expected if the olefin reactant possessed an alkyl substituent in close proximity to the double bond.

Since the remaining double bonds of the olefin do not enter into the reaction process, virtually any diolefin or polyolefin, regardless of the position of the remaining double bonds, is suitable for use in the practice of this invention. Because either double bond of the olefin reactant may react to a lesser or greater degree with the halogenated isocyanurate, the technique herein employed is likely to produce a mixture of products. Furthermore when employing di- or tri-halogenated isocyanurate reactants, mixtures of products each differing in the number of olefin reactant remnants present in the product may be formed.

Synthesis of the compounds of this invention is accomplished by contacting the two hereinabove described reactants or mixtures thereof, optionally in the presence of an inert solvent. It is possible to contact the halogenated isocyanurate reactant with an excess amount of olefinic reactant in which case no solvent is required. Preferably the reaction is conducted in an unreactive solvent in which the halogenated isocyanurate is at least partially soluble. Representative of such preferred solvents are chlorobenzene and other unreactive halogenated aromatic solvents. Common unsubstituted aliphatic solvents are generally not suitable for purposes of this invention.

The reaction is carried out in any reaction vessel suitably designed to contain the reactants and products under the conditions of the reaction. Elevated temperatures or pressures are not required. Normally temperatures from about 0° C. to about 132° C. are sufficient but higher or lower temperatures may be used depending on the olefin and solvent used. Reaction may occur upon contacting of the two reactants. If less reactive reactants are utilized the reactants may be heated and mixed at an elevated temperature until reaction is substantially complete. If more reactive reactants are utilized the reaction may be slowed by cooling the reaction mixture and/or combining the reactants slowly over an extended time period.

The mole ratio range of olefinic reactant to halogenated isocyanurate reactant may range from as low as about 1 to 1 in the case where the halogenated isocyanurate reactant is mono-halogenated, to large excesses of olefinic reactant, e.g., about 12 to 1. When reacting a tri-halogenated isocyanurate reactant the mole ratio range is preferably at least about 3 to 1. Lower ratios of olefinic reactant, i.e., less than about 3 to 1 may also be suitable when the halogenated isocyanurate reactant does not completely dissolve in the solvent used. Optimum ratios of reactants will vary with the choice of reactants and solvents. Such optimum ratio of reactants may easily be determined according to the methods of normal chemical practice.

SPECIFIC EMBODIMENTS OF THE INVENTION

The invention having been described, the following examples are provided to further illustrate the method of synthesis used to produce compounds of this invention and are not to be construed as limiting the invention.

EXAMPLE 1

Tri-(2-chloro-3-butenyl)isocyanurate

Trichloro isocyanurate (23 g) was added to 500 ml of chlorobenzene placed in a 1-liter, three-necked flask previously flushed with dry nitrogen, and equipped with a mechanical stirrer, dip tube, and an exit condenser. Excess 1,3-butadiene was added by being bubbled through this mixture at ambient temperature over a time period of approximately 2 or 3 hours. An exothermic reaction was observed upon initial addition of the 1,3-butadiene. After completion of 1,3-butadiene addition a small amount of unreacted trichloro isocyanurate remained. The reaction mixture was heated to the boiling point and the remaining solids removed by filtration. Removal of solvent by distillation left a viscous liquid having the following analysis:

| Tri-(2-chloro-3-butenyl)isocyanurate | %C | %H | %N | %Cl |
| --- | --- | --- | --- | --- |
| calculated | 45.6 | 4.6 | 10.7 | 26.9 |
| found | 44.9 | 4.4 | 10.7 | 27.0 |

Analysis by infrared spectrometry showed olefin addition had occurred and confirmed the identity of the product as primarily tri-(2-chloro-3-butenyl)isocyanurate.

EXAMPLE 2

Addition Product of Trichloro Isocyanurate and Dicyclopentadiene

Chlorobenzene solvent was dried by contacting with phosphorus pentoxide and then filtered. Solid trichloro isocyanurate (15.8 g) was added to a 1-liter flask equipped with a dropping funnel, stirrer and thermometer containing about 250 ml of the dried and filtered chlorobenzene.

Commercially obtained dicyclopentadiene (95 percent purity), was also dried by contacting with phosphorus pentoxide and filtered. An excess amount, approximately 52 ml, having a density of 0.93 g/cc, was added to the dropping funnel containing approximately 100 ml of dried and filtered chlorobenzene. The mixture was added slowly with stirring over approximately 1 hour to the trichloro isocyanurate mixture at ambient temperature.

An exothermic reaction was observed on addition of the dicyclopentadiene mixture and the solid trichloro isocyanurate dissolved slowly over the course of dicyclopentadiene addition. A maximum temperature of 57° C.–58° C. was noted during the course of dicyclopentadiene addition.

The reaction mixture was heated to approximately 100° C. and maintained at that temperature with stirring for approximately 16 hours. During the course of the heating the solution changed color from an initial pale yellow to dark green ultimately leaving a clear green solution.

After cooling, the solution was filtered leaving no observable precipitate and the solvent removed under a vacuum. Approximately 35 g of a dark green solid was isolated. The solid was found to be soluble in methylene chloride and chlorobenzene but insoluble in diethyl ether, ethanol, and hexane. Recrystallization from methylene chloride/hexane solution produced a light green solid.

Incipient decomposition of the solid was observed to begin at approximately 152° C. Analysis by infrared spectroscopy indicated olefin addition had occurred. The solid comprised a mixture of mono-, di- and tri-substituted products having the following formulas and names:

| Substituent | Product formed |
| --- | --- |
| (structure with H, Cl, H substituents) | 1-; 1,3-bis; or 1,3,5-tris(5-chloro-3a,4,5,6,7,7a-hexahydro-4,7-methano-1H-inden-5-yl)-s-triazine-2,4,6-trione |

-continued

| Substituent | Product formed |
|---|---|
| [structure with H, Cl, H] | 1-; 1,3-bis; or 1,3,5-tris(6-chloro-3a,4,5,6,7,7a-hexahydro-4,7-methano-1H-inden-5-yl)-s-triazine-2,4,6-trione |
| [structure with H, Cl, H] | 1-; 1,3-bis; or 1,3,5-tris(2-chloro-2,3,3a,4,7,7a-hexahydro-4,7-methano-1H-inden-2-yl)-s-triazine-2,4,6-trione |
| [structure with H, Cl, H] | 1-; 1,3-bis; or 1,3,5-tris(1-chloro-2,3,3a,4,7,7a-hexahydro-4,7-methano-1H-inden-2-yl)-s-triazine-2,4,6-trione |

EXAMPLE 3

Addition Product of Trichloro Isocyanurate and 2,5-Cyclohexadiene-1,4-dione

Repeating the reaction conditions of Example 1 using as a diene excess 2,5-cyclohexadiene-1,4-dione added from a dropping funnel results in an exothermic reaction and production of 1,3,5-tris(6-chloro-2,5-dioxo-3-cyclohexen-1-yl)-s-triazine-2,4,6)-trione, along with mono- and di-substituted reaction products.

What is claimed is:

1. A halogenated alkenyl isocyanurate compound of the formula

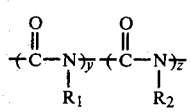

wherein:
(a) $R_1$ is selected from

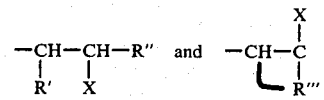

wherein R' is hydrogen or a $C_{1-10}$ radical selected from alkyl, alkenyl and oxo-, halo- or alkyl-substituted derivatives thereof; R'' is a $C_{2-10}$ radical selected from alkyl, alkenyl and oxo-, halo- or alkyl-substituted derivatives thereof, provided that at least one of R' or R'' is alkenyl or an oxo-, halo- or alkyl-substituted derivative thereof; R''' is a $C_{3-10}$ divalent radical containing ethylenic unsaturation selected from acyclic, cyclic and multicyclic alkenediyls and alkyl-, halo- or oxo-derivatives thereof; X is halogen;

(b) $R_2$ is a $C_{1-8}$ radical selected from alkyl, haloalkyl and aryl; and (c) y is an integer from 1 to 3; and z is an integer from 0 to 2, provided that y+z equals 3.

2. A compound according to claim 1 wherein X is chlorine.

3. A composition of matter comprising a mixture of compounds of claim 2.

4. A compound according to claim 2 wherein y is 3.

5. A compound according to claim 4 that is 1,3,5-tris(6-chloro-2,5-dioxo-3-cyclohexen-1-yl)-s-triazine-2,4,6-(1H,3H,5H)-trione.

6. A compound according to claim 4 which is tri-(2-chloro-3-butenyl)isocyanurate.

* * * * *